US008703827B2

(12) United States Patent
Jenkins

(10) Patent No.: US 8,703,827 B2
(45) Date of Patent: *Apr. 22, 2014

(54) THERAPEUTIC FOAM

(75) Inventor: William John Jenkins, London (GB)

(73) Assignee: BTG International Ltd. (GB)

( * ) Notice: Subject to any disclaimer, the term of this patent is extended or adjusted under 35 U.S.C. 154(b) by 239 days.

This patent is subject to a terminal disclaimer.

(21) Appl. No.: 11/914,192

(22) PCT Filed: May 12, 2006

(86) PCT No.: PCT/GB2006/001754
§ 371 (c)(1),
(2), (4) Date: May 30, 2008

(87) PCT Pub. No.: WO2006/120469
PCT Pub. Date: Nov. 16, 2006

(65) Prior Publication Data
US 2009/0124704 A1    May 14, 2009

(30) Foreign Application Priority Data

May 13, 2005  (GB) .................................. 0509824.9
Aug. 24, 2005  (GB) .................................. 0517361.2

(51) Int. Cl.
*A01N 31/14*    (2006.01)
(52) U.S. Cl.
USPC .......................................... 514/723; 514/769
(58) Field of Classification Search
USPC .................................................. 514/723, 769
See application file for complete search history.

(56) References Cited

U.S. PATENT DOCUMENTS

| | | |
|---|---|---|
| 2,630,183 A | 3/1953 | Foutz |
| 2,724,383 A | 11/1955 | Lockhart |
| 3,698,453 A | 10/1972 | Morane et al. |
| 3,767,085 A | 10/1973 | Cannon et al. |
| 3,955,720 A | 5/1976 | Malone |
| 3,970,219 A | 7/1976 | Spitzer et al. |
| 4,019,657 A | 4/1977 | Spitzer et al. |
| 4,040,420 A | 8/1977 | Speer |
| 4,127,131 A | 11/1978 | Vaillancourt |
| 4,276,885 A | 7/1981 | Tickner et al. |
| 4,292,972 A | 10/1981 | Pawelchak et al. |
| 4,328,107 A | 5/1982 | Wright |
| 4,466,442 A | 8/1984 | Hilmann et al. |
| 4,538,920 A | 9/1985 | Drake |
| 4,718,433 A | 1/1988 | Feinstein |
| 5,048,750 A | 9/1991 | Tobler et al. |
| 5,064,103 A | 11/1991 | Bennett |
| 5,071,379 A | 12/1991 | Poizot |
| 5,084,011 A | 1/1992 | Grady |
| 5,141,738 A | 8/1992 | Rasor et al. |
| 5,368,231 A | 11/1994 | Brunerie |
| 5,425,366 A | 6/1995 | Reinhardt et al. |
| 5,425,580 A | 6/1995 | Beller |
| 5,454,805 A | 10/1995 | Brony |
| 5,542,935 A | 8/1996 | Unger et al. |
| 5,556,610 A | 9/1996 | Yan et al. |
| 5,623,085 A | 4/1997 | Gebhard et al. |
| 5,656,200 A | 8/1997 | Boettcher et al. |
| 5,676,962 A | 10/1997 | Garrido et al. |
| 5,733,572 A | 3/1998 | Unger et al. |
| 5,902,225 A | 5/1999 | Monson |
| 6,053,364 A | 4/2000 | van der Heijden |
| 6,536,629 B2 | 3/2003 | van der Heijden |
| 6,561,237 B1 | 5/2003 | Brass et al. |
| 6,572,873 B1 | 6/2003 | Osman et al. |
| 6,605,066 B1 | 8/2003 | Gravagna et al. |
| 6,942,165 B1 | 9/2005 | Osman et al. |
| RE38,919 E | 12/2005 | Garrido et al. |
| 7,025,290 B2 | 4/2006 | Osman et al. |
| 7,357,336 B2 | 4/2008 | Osman et al. |
| 2002/0031476 A1 | 3/2002 | Trevino et al. |
| 2002/0056730 A1 | 5/2002 | van de Heijden |
| 2002/0077589 A1 | 6/2002 | Tessari |
| 2002/0101785 A1 | 8/2002 | Edwards et al. |
| 2004/0156915 A1 | 8/2004 | Harman et al. |
| 2005/0002873 A1* | 1/2005 | Harman et al. .................. 424/47 |
| 2006/0049269 A1 | 3/2006 | Osman et al. |
| 2006/0062736 A1 | 3/2006 | Wright et al. |
| 2006/0280690 A1 | 12/2006 | Wright et al. |

(Continued)

FOREIGN PATENT DOCUMENTS

| | | |
|---|---|---|
| CA | 1 232 837 | 2/1988 |
| DE | 26 08 771 A1 | 9/1976 |

(Continued)

OTHER PUBLICATIONS

69th Medical Seminar Evening of the Van-Swieten Society in the District Hospital of Villach, pp. 1-2, Meeting of Oct. 30, 1959.
"Sulfaproxyline"; The Merck Index, an Encyclopedia of Chemicals, Drugs, and Biologicals, 12th Edition; p. 1527; 1996.
Aizman, I.M., "On the Treatment with Sclerosal Agents of Patients with Varicose Lower Extremities," Xupyprus, pp. 46-49, 1964.
Anon, "New Drugs," Australian Prescriber, vol. 25, No. 1, pp. 20-23, 2002.
Baniel, A. et al., "Foaming Properties of Egg Albumen with a Bubbling Apparatus Compared with Whipping," J. Food Science, vol. 62(2): 377-381, 1997.
Baridevic, J., "Varicosclerozation in Phlebological Practice"; The Journal for Doctors, in Clinic and Practice; vol. XXI, No. 3, pp. 126-136; Jan. 11, 1989.
Barry et al., "Atmosphere, weather, and climate," Taylor & Francis, 3rd Ed., p. 25 (1976).

(Continued)

*Primary Examiner* — Jason M Sims
*Assistant Examiner* — Ibrahim D Bori
(74) *Attorney, Agent, or Firm* — Finnegan, Henderson, Farabow, Garrett & Dunner, LLP

(57) ABSTRACT

A foam for the treatment of varicose veins is disclosed, comprising a sclersosant solution, e.g. polidocanol, foamed with a gas mixture which includes greater than 41% of a lipid soluble gas such as xenon. The aim is to provide a foam which may be injected into a varicose vein in large quantities because the gas component is dissipated quickly after the foam has acted on the varicose vein.

6 Claims, No Drawings

(56) References Cited

U.S. PATENT DOCUMENTS

| | | |
|---|---|---|
| 2007/0003488 A1 | 1/2007 | Wright et al. |
| 2007/0003489 A1 | 1/2007 | Wright et al. |
| 2007/0031345 A1 | 2/2007 | Harman et al. |
| 2007/0031346 A1 | 2/2007 | Harman et al. |
| 2007/0104651 A1 | 5/2007 | Wright et al. |
| 2008/0145401 A1 | 6/2008 | Osman et al. |
| 2008/0274060 A1 | 11/2008 | Wright et al. |

FOREIGN PATENT DOCUMENTS

| | | | |
|---|---|---|---|
| DE | 3048744 | 7/1982 | |
| DE | 3050812 | 3/1985 | |
| DE | 8704600 | 11/1987 | |
| DE | 3417182 | 1/1989 | |
| EP | 00 11 381 | 5/1980 | |
| EP | 0054728 | 6/1982 | |
| EP | 0077752 | 4/1983 | |
| EP | 0123235 | 10/1984 | |
| EP | 0131540 | 1/1985 | |
| EP | 0217582 | 4/1987 | |
| EP | 0324938 | 7/1989 | |
| EP | 0359246 | 3/1990 | |
| EP | 0564505 | 10/1993 | |
| EP | 0586875 | 3/1994 | |
| EP | 06 13 836 A1 | 9/1994 | |
| EP | 0656203 | 6/1995 | |
| EP | 0997396 | 5/2000 | |
| EP | 1716871 | 2/2006 | |
| ES | 2 068 151 | 4/1995 | |
| FR | 1 547 768 | 11/1968 | |
| FR | 2 672 038 | 7/1992 | |
| FR | 2 775 436 | 9/1999 | |
| GB | 2 369 996 | 6/2002 | |
| JP | 8-235664 | 9/1996 | |
| JP | 10-81895 | 3/1998 | |
| WO | WO 92/05806 | 4/1992 | |
| WO | WO 92/11873 | 7/1992 | |
| WO | WO 93/05819 | 4/1993 | |
| WO | WO 94/21384 | 9/1994 | |
| WO | WO 95/00120 | 1/1995 | |
| WO | WO 96/08227 | 3/1996 | |
| WO | WO 96/25194 | 8/1996 | |
| WO | WO 96/38180 | 12/1996 | |
| WO | WO 97/13585 | 4/1997 | |
| WO | WO 99/43371 | 9/1999 | |
| WO | WO 00/24649 | 5/2000 | |
| WO | WO 00/72821 A1 * | 7/2000 | ............... A61K 9/12 |
| WO | WO 00/66274 | 11/2000 | |
| WO | WO 00/72821 | 12/2000 | |
| WO | WO 00/78629 | 12/2000 | |
| WO | WO 02/058834 | 8/2002 | |
| WO | WO 03/013475 | 2/2003 | |
| WO | WO 2004/047969 | 6/2004 | |
| WO | WO 2005/115484 A1 | 8/2005 | |

OTHER PUBLICATIONS

Battezzati, M. et al., "Treatment of Lower Limb Varices with Multiple Endermic Ligations and Sclerosant Injections Combined or not with Stripping of the long Saphenous Vein's higher region," Minerva Chirurgica, pp. 936-939, 1952.

Bayeux, R., "Comparative Resistance of Dog and Rabbit to Intravenous Injection of Oxygen," Compt. Rend. vol. 156, pp. 1329-1331, 1913.

Belcaro, G. et al., "Treatment of Superficial Venous Incompetence with the Savas Technique," Journal des Maladies Vasculaires (Paris), vol. 16, pp. 23-27, 1991.

Belcaro, G. et al., "Treatment of Superficial Venous Incompetence with a Hemodynamic Technique on an Outpatient Basis: The SAVAS Technique," Vascular Surgery, pp. 32-36, Jan./Feb. 1992.

Belcaro, G.; "Micro-sclerotherapy"; Sclerotherapy in Venous Disease; pp. 89-95; 2002.

Bergan, J., "Classic Paper: Nicht-Operative Varizenverödung Mit Varsylschaum," Abstract, Venous digest, 2006.

Bernbach, H.R., "Sclerosing Injections Using the SIGG Method," SociétéFrançaise de Phlébologie, vol. 44, No. 1, pp. 31-36, 1991.

Berson, I., "Sclerotization or surgery in the treatment of varicose veins of the inferior extremities," University Clinic for dermato-venerology, Lausanne, pp. 485-490, 1960.

Biegeleisen, H. ,"Fatty Acid Solutions for the Injection Treatment of Varicose Veins," Annals of Surgery, vol. CV, pp. 610-615, 1936.

Biegeleisen, K. et al., "Inadvertent Intra-Arterial Injection Complicating Ordinary and Ultrasound-Guided Sclerotherapy," Phlebology, vol. 19, pp. 953-958, 1993.

Blenkinsopp, W.K., "Choice of Sclerosant: An Experimental Study," Angiologica, vol. 7, pp. 182-186, 1970.

Blenkinsopp, W.K., "Effect of Injected Sclerosant (Tetradecyl Sulphate of Sodium) on Rat Veins," Angiologica, vol. 5, No. 6, pp. 386-396, 1968.

Bock, M.D.H.-D.; "Varicosis and its Therapy"; Ärztliche Praxis; vol. XIX, No. 60, pp. 2146-2148; Jul. 1967.

Bodian, E.L., "Techniques of Sclerotherapy for Sunburst Venous Blemishes," J. Dermatol. Surg. Oncol., vol. 11, No. 7, pp. 696-704, Jul. 1985.

Breu, F.X. et al. ;"Duplex Scanning of Lipedema and Lymphedema"; pp. 309-313; Scope on Phlebology and Lymphology; vol. 8; Issue 3/4; Dec. 2001.

Brucke, H., et al., "Die kombinierte Schaumverodung der Varizen," Wiener Medizinische Wochenschrift, vol. 104, No. 1, pp. 111-113, Jan. 1954 (Eng. Translation—"The combined foam sclerosis of varices").

Butler Studies to Date, "Summary of the Butler gas physiology studies to date (Jun. 13, 2003)," pp. 1-12.

Cabrera, J., "Echo-Sclerotherapy of Long Saphenous Veins and Venous Malformations with Sclerosing Agents in Microfoam Long-Term Outcomes," A Joint Meeting of the Canadian Society of Phlebology and The Sclerotherapy Society of Australia, The Transpacific Phlebology Forum, Jun. 27-Jul. 1, 1997, Sclerotherapy Society, p. 12.

Cabrera, J. et al., "Sclerosants in Microfoam—A New Approach in Angiology," International Angiology, vol. 20, pp. 322-329, 2001.

Cabrera, J. et al., "Treatment of Venous Malformations with Sclerosant in Microfoam Form," Arch Dermatol, vol. 139, 2003, 1409-1416.

Cabrera, J. et al., "Treatment of Varicose Long Saphenous Veins with Sclerosant in Microfoam Form: Long-Term Outcomes"; Phlebology, No. 15, pp. 19-23; 2000.

Cabrera, J. et al., "Treatment of Varicose Long Saphenous Veins with Sclerosant in Microfoam Form: Long-Term Outcomes"; vol. 8, Issue 3/4, pp. 293-298, 2001.

Cabrera-Garrido, J. et al., "Escleroterapia en Micorespuma : Nuevo Concepto en Escleroterapia. Resultados a Lorgo Plazo."; Revista Panamericana de Flebologia y Lonfologia; No. 34; pp. 29-37; Sep. 1999.

Cabrera-Garrido, J. et al., "Elargissement de Limites de la Sclérothérapie: Nouveaux Produits Sclérosants"; Phlébologie; vol. 50, No. 2 ; pp. 181-188 ; 1997. (Engl. Translation—"Extending the Limits of Sclerotherapy: New Sclerosing Products").

Cabrera-Garrido, J. et al., "New Pharmaceutical Form of Sclerosants: Use in the Treatment of Inoperable Venous Malformations," Engl. Translation of Spanish Poster, May 1997.

Cabrera-Garrido, J.R. et al., (English translation) "New Method of Effecting Sclerosis in Varices of the Trunk Veins" Vascular Pathology, vol. 1, No. 4, Oct. 1995.

Camara, D.S. et al., "The Hemodynamic Effects of the Sclerosant Sodium Morrhuate in Dogs," Surgery—Gynecology and Obstetrics, vol. 161, No. 4, pp. 327-331, Oct. 1985.

Caprini, J. et al., "Direct Factor X Inhibition," American College of Phlebology, MarcoIsland, FL, Nov. 7-9, 2008.

Caprini, J. et al., "DVT Prophylaxis: What Every Physician Should Know," American College of Phlebology, MarcoIsland, FL, Nov. 7-9, 2008.

Cavezzi, A. et al., "The Use of Sclerosant Foam in Sclerotherapy: possibilities and limits," Management of Venous Disease in the New Millennium, pp. 16-17, Jul. 2000.

(56) References Cited

OTHER PUBLICATIONS

Cavezzi, A. et al., "Treatment of Varicose Veins by Foam Sclerotherapy: Two Clinical Series," The Venous Forum of the Royal Society of Medicine and Societas Phlebologica Scandinavica, vol. 17, No. 1, pp. 13-18, Nov. 2002.

Cavezzi, A., "Duplex Guided Sclerotherapy of Long and Short Saphenous Vein With Sclerosing Foam," In Foam Sclerapy State of Art, ed. J.P. Heneriet, Editions Phlebologique Francais pp. 61-71 (2002).

Cho, Kyung J., "Carbon Dioxide Angiography," http://www.emedicine.com/radio/TOPIC870.HTM, p. 1-17 (2008).

Cockett, F.B., "Arterial Complications during Surgery and Sclerotherapy of Varicose Veins," *Phlebology*, vol. 1, pp. 3-6, 1986.

Comerota, A., "Management of Acute DVT," *American College of Phlebology*, 22$^{nd}$ Annual Congress, Marco Island, Florida, Nov. 6-9, 2008.

Davy, A. et al., "Ostial Incompetence: Sclerosis or Resection?," *Phlébologie*, vol. 39, No. 1, pp. 35-45, 1986.

De L'Académie des Sciences, Conformément a Une Decision de L'Académie, pp. 890-892, 1930.

de Somer-Leroy, R. et al., "Echographie du Creux PoplitéRecherche D'Une ArterioléPetite Saphéne Avant Sclérothérapie," SociétéFrançaise de Phlébologie, vol. 44, No. 1, pp. 69-78, 1991.

de Takats, G. et al., "Aneurysms: General Considerations," *Angiology, The Journal of Vascular Diseases*, vol. 5, No. 3, pp. 173-208, Jun. 1954.

de Takats, G. et al., "Division of the Popliteal Vein in Deep Venous Insufficiency of the Lower Extremities," *Society for Vascular Surgery Issue*, vol. 29., No. 3, pp. 342-354, Mar. 1951.

de Takats, G. et al., "Ligation of the Saphenous Vein," A report on Two Hundred Ambulatory Operations, *Archives of Surgery*, vol. 26, No. 1, pp. 72-88, Jan. 1933.

de Takats, G. et al., "The Injection Treatment of Varicose Veins," *Surgery, Gynecology and Obstetrics*, vol. L, No. 3, pp. 545-561, Mar. 1930.

de Takats, G., "Ambulatory Ligation of the Saphenous Vein," The Journal of the American Medical Association, vol. 94, No. 16, pp. 1194-1197, Apr. 19, 1930.

Decoppet, R.W., "The Sclerotherapy of Varices with Thrombophilic Patients," *Swiss Medical Weekly Journal*, 86$^{th}$ year, No. 20, pp. 509-513, May 19, 1956.

de Groot, W.P., "Treatment of Varicose Veins: Modern Concepts and Methods," *The Journal of Dermatologic Surgery and Oncology*, vol. 15, No. 2, pp. 191-198, Feb. 1989.

Dodd, H., "The 'Stripping' Operation for Varicose Veins," *The Postgraduate Medical Journal*, vol. 31, pp. 73-78, 1955.

Dodd, H., "Varicose Veins and Venous Disorders of the Lower Limb," *The Irish Journal of Medicinal Science*, Sixth Series, No. 400, pp. 162-174, Apr. 1959.

Dodd, H., "Varicose Veins and Venous Disorders of the Lower Limb," The Proceedings of the Cardiff Medical Society, pp. 28-45, 1962.

Dodd, H., "Vulval Varicose Veins in Pregnancy," Tensile Strength of Arterial Grafts, *British Medical Journal*, pp. 831-832, Mar. 28, 1959.

Durant, T.M. et al., "The Safety of Intravascular Carbon Dioxide and its Use for Roentgenologic Visualization of Intracardiac Structures," *Annals of Internal Medicine*, vol. 47, No. 2, pp. 191-201, Aug. 1957.

Edmonds-Seal, J. et al., "Air Embolism," *Anaesthesia*, vol. 26, No. 2, pp. 202-208, Apr. 1971.

Efuin. S. et al., "Oxygen Parameters of Blood and Tissues during Intravascular Oxygenation of the Organism," *Eksperimental'naya Khirurgiya i Anesteziologiya*, vol. 5, pp. 71-74, 1974.

Eichenberger, H., "Results of the Sclerotherapy of Varicose Veins with Hydroxypolyaethoxy-Dodecan," *Zentralblatt für Phlebologie*, vol. 8, pp. 181-183, 1969.

Elias, S., "Is There a Leak? Where Is the Leak? How Many Leaks? Which Leak Do I Fix?," *American College of Phlebology*, Marco Island, FL, Nov. 7-9, 2008.

Emerson, E.C., "A Reappaisal of the Injection Treatment of Varicose Veins," *Angiology the Journal of Vascular Diseases*, vol. 14, No. 1, pp. 8-13, Jan. 1963.

English translation of Opposition to the European Patent EP 1 180 015 B1, filed Sep. 21, 2006.

Ershov, Y.A. et al., "Variant of an Operation on Enlarged Veins of the Oesophagus and Cardia in Patients with Portal Hypertension Syndrome," *Surgery—Monthly Science Practice Journal*, Ministry of Health of the U.S.S.R. All-Union Scientific Society of Surgeons, pp. 46-49, Sep. 1991.

Fabi, M. et al., "Un Nuovo Metodo di Terapia Sclerosante nel Trattamento delle Varici," *L'Arcispedali S. Anna di Ferrera*, Book 1, pp. 351-354, 1964.

Farina, M.A. et al., "Outpatient Treatment of Varicose Vein Segments: Two Techniques Compared," *Phlébologie*, pp. 1070-1071, 1989.

Fegan, G., "The Treatment of Venous Insufficiency During Pregnancy," *Varicose Veins—Compression Sclerotherapy*, Chapter VII, pp. 93-98, 1967.

Fegan, W.G. et al., "A Modern approach to the injection treatment of varicose veins and its applications in pregnant patients," *American Heart Journal*, vol. 68, No. 4, pp. 757-764, Oct. 1964.

Fegan, W.G., "Conservative Treatment of Varicose Veins," *Progr. Surg.*, vol. 11, pp. 37-45, 1973.

Fegan, W.G., "Continuous Uninterrupted Compression Technique of Injecting Varicose Veins," *Proceedings of the Royal Society of Medicine*, vol. 53, No. 7, pp. 837-840, Jul. 1960.

Feied, C.F., MD, FACEP; "Mechanism of Action of Sclerosing Agents and Rationale for Selection of a Sclerosing Solution," *American Vein Institute*; (8 pages) 1996.

Ferguson, L.K., "Ligation of Varicose Veins, Ambulatory Treatment Preliminary to Sclerosing Injections," *Annals of Surgery*, vol. CII, pp. 304-314, 1935.

Fluckiger, P. et al., "Beitrag zur Technik der ambulanten Varizenbehandlung," *Die Medizinische Welt*, No. 12, pp. 617-621, 1963.

Fluckiger, P. et al., "Physical and Biological Pathogenetic Components of Varicosis," *Schweizer Medizinische Wochenschrift*, No. 45, 1963 (Engl. Transl.).

Fluckiger, P., "Der Erythem-Test im Rahmen der präoperativen Varizenuntersuchung," Praktische *VASA*, vol. 3, No. 2, pp. 198-199, 1974.

Fluckiger, P., "Intraoperative Varicosclerosation with Sodium Tetradecyl Foam in the Babcock Operation," *Zentralblatt für Phlebologie*, vol. 1, No. 6, pp. 514-518, Feb. 1967.

Fluckiger, P. et al., "Nicht-operative retrograde Varicenverödung mit Varsylschaum," *Schweizerische Medizinische Wochenschrift*, No. 48, pp. 1368-1370, 1956 (Engl. Title: "Non-Surgical Retrograde Sclerosis of Varicose Veins With Varsyl Foam").

Foote, R., "Treatment," Varicose Veins, Chapter 5, p. 65 and 86, 1949.

Foote, R.R., "Varicose Vein Problems in General Practice," *The Practitioner—Medical Etiquette*, vol. 179, No. 1069, pp. 59-66, Jul. 1957.

Fronek, H., "Treatment of Small Veins," American College of Phlebology 22$^{nd}$ Annual Meeting, Marco Island, FL, Nov. 6-9, 2008.

Frugis, E. et al., "Telangiectasia Sclerotherapy of the Lower Limbs," *Minerva Dermatologica*, Vo. 43, pp. 368-371, 1968.

Frullini, A "Foam Sclerotherapy: a review," *Phlebolymphology*, No. 40, p. 125-129, 2003.

Frullini, A. et al., "Sclerosing Foam in the Treatment of Varicose Veins and Telangiectases: History and Analysis of Safety and Complications," *Dermatol Surg*, vol. 28, No. 1, pp. 11-15, Jan. 2002.

Frullini, A., "New Technique in Producing Sclerosing Foam in a Disposable Syringe," *Dermatol Surg*, vol. 26, pp. 705-706, 2000.

Frullini, A., "Sclerosing Foam," American College of Phlebology 22$^{nd}$ Annual Meeting, Marco Island, FL, Nov. 7-9, 2008.

Galata, G. "Intravenous Injection of Oxygen in Dogs," *Archivio di Fisiologia*, vol. 21, pp. 331-350, 1923.

Garcia Mingo J., "'Foam Medical System': a new technique to treat varicose veins with foam," in Foam Sclerotherapy State of the Art, ed. J.P. Henriet, Editions *Phlébologique*, pp. 45-50, 2002.

Garcia Mingo, J., "Venous Sclerosis with Foam: 'Foam Medical System'," *Revista Española de Medicina y Cirugia Cosmética*, vol. 7, pp. 29-31, 1999.

Garrido, J., "Medicine: Microfoam sclerosants against venous illnesses," *Medical News*, p. 12-16, May 1997.

(56) References Cited

OTHER PUBLICATIONS

Gasparini, D., "Therapeutic embolization in pulmonary hemorrhage," *Radiologica Interventistica*, vol. 77, pp. 223-229, 1989.
German Nullity Action Complaint filed Jun. 27, 2001 (Engl. Transl.).
German Nullity Action First Brief filed Dec. 3, 2001.
German Nullity Brief filed Dec. 31, 2002 (Engl. Transl.).
German Nullity Action Kreisler Brief filed Jan. 27, 2003.
German Nullity Action Decision by German Court dated Feb. 4, 2003. (Engl. Transl.).
German Nullity Action Substantiation of Appeal to the Federal Court of Justice on Sep. 26, 2003 (Engl.Transl.).
German Nullity Action Reply to appeal dated Feb. 12, 2004 (Engl. Transl.).
German Nullity Appellant's statement dated Apr. 4, 2007 in German Nullity Appeal Proceedings BTG International Ltd.
German Nullity Judgment dated May 22, 2007, in German Nullity Appeal Proceedings BTG International Ltd., X ZR 56/03 (10 pgs.).
Gerson, L., "The Treatment of Varicose Veins, A Critical Study of Choice of Method," *Angiology*, The Journal of Vascular Diseases, vol. 13, No. 16, pp. 260-264, 1962.
Gibson, K., "Proprietary Polidocanol Endovenous Microfoam Bubble Embolization Does Not Cause Cerebral Injury," *American College of Phlebology*, Marco Island, FL, Nov. 7-9, 2008.
Gilje, O., "Injection Treatment of Varicose Veins," *Den norske lægeforening Norwegian Medical Association*, No. 17, pp. 1380-1381, Sep. 1963.
Gillesberger, W.; "The Equipment of the Dermatologist Working in the Field of Phlebology," *Journal for Skin Diseases*; vol. 44, No. 18, pp. 669-674; 1969.
Gillet, J.L., "Side Effects and Complications of Foam Sclerotherapy of the Great and Small Saphenous Veins: a Controlled and Multicentre Prospective Study Including 1025 Patients," *American College of Phlebology*, Marco Island, FL, Nov. 7-9, 2008.
Goldberg, D., "Nd: YAG laser treatment of spider veins," *Scope on Phlebology and Lympohology*, vol. 8, Issue 3/4, pp. 284-288, Dec. 2001.
Goldman, M.P. et al., Continuing medical education (Dermatologic surgery), "Treatment of Telangiectasia: a review," *Journal of the American Academy of Dermatology*, vol. 17, No. 2, Part 1, pp. 167-182, Aug. 1987.
Goldman, M.P., "Sclerotherapy Treatment of Varicose and Telangiectatic Leg Veins," *Clinical Methods for Sclerotherapy of Varicose Veins*, pp. 274-275, 290, 312 and 323, 1991.
Gorisch, V. et al., "Appearance of intravenously given radioactive oxygen in expired air," *Naunyn-Schmiedebergs Archiv fuer Experimentelle Pathologie und Pharmakologie*, vol. 238, pp. 106-107, 1960. Abstract.
Gorish, V. et al., "Expiration of labeled oxygen after intravenous insufflation," *Medicina Experimentalis*, vol. 1, pp. 333-338, 1959.
Graff, T.D. et al., "Gas Embolism: A Comparative Study of Air and Carbon Dioxide as Embolic Agents in the Systemic Venous System," *Am. J. Obst. & Gynec.*, pp. 259-265, Aug. 1959.
Grondin, L., "Echosclerotherapy of Saphenous Axis with Microfoam Agents," Abstracts form the 13th Annual Congress of the *American College of Phlebology*, Nov. 1999.
Grosse-Brockhoff, F. et al., "Carbon Dioxide as a Contrast Medium for use in Radiology of the Heart and Blood Vessels," *Fortschritte auf dem Gebiete der Röntgenstrahlen und der Nuklearmedizin*, vol. 86, No. 3, pp. 285-291, Mar. 1957.
Guex, J., "The French Polidocanol Registry on Long Term Side Effects: A Survey Covering 3357 Patient Years," *American College of Phlebology*, Marco Island, FL, Nov. 7-9, 2008.
Gunther, E., "On the indication and method of sclerotherapy," *Ärztliche Fortbildung*, vol. 22, pp. 1296-1298, Nov. 1961.
Gyorgy, B., "Visszérbetegség Másodlagos Szövödményeinek Kelelése," *Orvosi Hetilap*, vol. XCIX, No. 35, pp. 1215-1218, 1958. (Engl. Title : Treatment for Secondary Complications Resulting from Varicosity).

Handley, R.S., "The Treatment of Varicose Veins," *The Practitioner—Diseases of the Veins*, vol. 166, No. 993, pp. 228-235, Mar. 1951.
Harkins, H. et al., "Embolism by Air and Oxygen: Comparative Studies," *Proceedings of the Society for Experimental Biology and Medicine*, vol. 32, pp. 178-181, Oct.-Jun. 1934-1935.
Harper, K.E,, "Advances in Therapy for Venous Disease Ambulatory Phlebectomy 'Cleaning Up Branch Varicose veins'," *American College of Phlebology*, Marco Island, FL, Nov. 7-9, 2008.
Hauer, G., "Diagnostic and Surgical Treatment of Varicose Veins," *Herz*, vol. 14, No. 5, pp. 274-282, 1989.
Hauser, A. et al., "Prophylaxis of phlebitis and treatment of varices during pregnancy," *Schweizerische Medizinische Wochen-schrift*, 84th year, No. 1, pp. 13-14, Jan. 2, 1954.
Henriet, J.P., "One Year of Daily Application of Sclerotherapy (Reticular Veins and Telangiectases) Using Polidocanol Foam: Feasibility, Results, Complications," *Phlebologie*, vol. 50, No. 3, pp. 355-360, 1997.
Henriet, J.P., "History of Foam," *Foam Sclerotherapy State of the Art*, ed. J.P. Henriet, Editions Phlebologiques Francaises, pp. 13-15, 2002.
Henschel, O., "Die Varizenverördung—Verördungstherapie mit Aethoxysklerol—Kreussler," p. 22; 1968.
Hess, H., "Digital Subtraction Arteriography with Carbon Dioxide: an alternative to arteriography of the extremities with iodine-containing contrast media," *Forlschr. Röntgenstr.*, vol. 153, No. 3, pp. 233-238, 1990.
Heyerdale, W. et al., "Management of Varicose Veins of the Lower Extremities," *Annals of Surgery*, vol. 114, pp. 1042-1049, 1941.
Hill, D., "Comparison of Sclerosant Foam Stability by Foam Composition," *American College of Phlebology*, Marco Island, FL, Nov. 7-9, 2008.
Hobbs, J.T., "Compression Sclerotherapy in Venous Insufficiency," *Acta Chir Scand Suppl.*, vol. 544, pp. 75-80, 1988.
Hobbs, J.T., "Surgery and Sclerotherapy in the Treatment of Varicose Veins," *Arch. Surg.*, vol. 109, pp. 793-796, Dec. 1974.
Holzegel, K., "On Sclerosing Agents for Varicose Veins," *Zentralblatt für Phlebologie*, vol. 9, pp. 43-53, 1970.
Hordegen, K.M., "Ulcus cruris—ambulante Behandlung and Ergebnisse," *Schweiz. Med. Wschr.*, vol. 119, No. 37, pp. 1264-1269, 1989.
Hubner, A., *Der Chirurg*, Journal for All Fields of Surgical Medicine, 26th Year of Edition, 1955.
Jaeger, F., "Primary or Secondary Varicose Veins," *Die Medizinische*, No. 36, pp. 1237-1240, Sep. 1955.
Jaeger, F., "Varicose Veins," *Deutsche Medizinische Wochenschrift*, 83rd year of edition, No. 30, p. 1295, Jul. 1958.
Jaeger, P.,, "The Current Treatment Standard or Crural Ulcer and Varices," *Deutsche Medizinische Wochenschrift*, 77th year of edition, No. 14, pp. 421-425, Apr. 1952.
Jausion, H., "Glycerine Chromee et Sclerose des Ectasies Veineuses," *La Presse Medicale*, No. 53, pp. 1061-1063, May 1933.
Jung, R., "Injection treatment of varicose veins," *Praxis*, pp. 195-198, 1950.
Karmazsin, L. et al., "Experimental study of lipid peroxidation following intravenous oxygen," *Kiserletes Orvostudomany*, vol. 39, No. 5, pp. 342-348, 1987.
King, T., "How Safe Is High Energy Endovenous Ablation?," *American College of Phlebology 22nd Annual Meeting*, Marco Island, FL, Nov. 6-9, 2008.
Knight, R.M. et al., "Ultrasonic guidance of injections into the superficial venous system," *Phlebology*, pp. 339-341, 1989.
Koistinen, P., "Eräitä näkökohtia alaraajojen laskimon-laajentumien hoidosta ja ennusteesta," *Duodecim*, vol. LXXII, No. 12, pp. 1000-1015, 1956.
König, T. et al., "CO2 Angiography: Measurement of Vascular Gas Filing and Evaluation of Parameters influencing Gas Injection using a Circulatory System Model," *Biomedizinische Technik*, vol. 36, No. 11, 266-270, 1991.
Krusch, M.P., "Insurance and Coding for the Phlebology Practice," Session 107, *American College of Phlebology*, Marco Island, FL, Nov. 7-9, 2008.

(56) References Cited

OTHER PUBLICATIONS

Kunkel, F., *Münchener Medizinische Wochenschrift*, 95th year of edition, vol. 30, No. 44, p. 53, 1953.
Leidinger, H., "Verizenverodung mit Air-Block-Technik (Varicocid plus Varicosidschaum," *Medizinische Klinik*, pp. 1183-1184, 1954 (Eng. Translation—"Sclerosation with air-block technique (Varicocid plus Varicocid foam").
Lemaire, A., et al., "Action de l'oxygene intra-arteriel sur le cholesterol sanguin," *Therapie*, vol. 13, pp. 395-399, 1958 (Eng. Translation—"Effect of Intra-arterial oxygen injection on blood cholesterol").
Leonhardt, H., "Uber die Behandlung ausgedehnter Krampfaderbildungen mit Ligatur der V. saphena und Varicocid-Injektion durch distal eingefuhrten Ureterenkatheter," *Ärztliche Wochenschrift*, vol. 7, No. 3, pp. 56-58, Jan. 1952 (Eng. Translation—"On the Treatment of Extensive Formation of Varicose Veins with Ligature of the v. Saphena and Varicoid Injection Through Distally Inserted Ureteral Catheter").
Leu, H.J. et al., "Die kombiniert chirurgisch-sklerosierende ambulante Behandlung der Saphenavarizen," *Schweizerische Rundschau für Medizin*, vol. 1, No. 61, pp. 1360-1364, Oct. 31, 1972 (Eng. Translation—"The Combined Surgical-Sclerotic Ambulatory Treatment of Saphenous Varicose Veins").
Leu, H.J. et al., "The Modern Conception of Therapy of Varicose Veins," *Angiology*, The Journal of Vascular Diseases, vol. 15, No. 9, pp. 371-378, Sep. 1964.
Leun, W. et al., Die Grenzen und Gefahren der Varizen-verodung, *Deutsche Medizinische Wochenschrift*, No. 7, pp. 257-260, Feb. 18, 1955 (Eng. Translation—"The Limits and Risks of the Sclerotherapy of Varicose Veins").
Lockhart-Mummery, H.E. et al., "Varicose Ulcer—A Study of the Deep Veins with Special Reference to Retrograde Venography," *The British Journal of Surgery*, vol. XXXVIII, No. 151, pp. 284-295, Jan. 1951.
Luke, J.C. et al., "Factors in the Improvement of Results in Varicose Vein Surgery," *Canadian Journal of Surgery*, vol. 6, No. 2, pp. 145-148, Apr. 1963.
Luke, J.C., "The Management of Recurrent Varicose veins," *Surgery, Original Communications*, vol. 35, No. 1, pp. 40-44, Jan. 1954.
Maerz, F., "Nil nocere!: Life-Threatening anaphylactic Incidents in Connection with Sclerosing of Varicose Veins," *Munchener Medizinische Wochenschrift*, vol. 27, No. 35, 1954.
MacPherson, A.I.S., "The Treatment of Varicose Veins," *The Practitioner—Diseases of the Veins*, vol. 183, No. 1093, pp. 11-18, Jul. 1959.
Mairano, M., "Metodo combinato chirurgico-sclerosante o metodo sclerosante semplice nel trattamento delle varici essenziali?" *Minerva Chirurgica*, vol. VI, No. 16, pp. 244-247, May 1951 (Eng. Translation—"Combined surgery and aclerosing method or simple sclerosing method in the treatment of primary varices").
Malyugin, E.F. et al., "Influence exerted on the liver by the intraportal administration of oxygen," *Farmakologiya*, vol. 37, No. 2, pp. 183-186, 1974.
Marmasse, J., "Les injections sclerosantes dans la crosse des veines saphenes. Explotation, Injection, Critique," *La Semaine des Hopitaux*, vol. 36, No. 17, pp. 1086-1095, Apr. 1960 (Eng. Translation—"Sclerosing Injections in the Saphenofemoral Junction of the Saphenous Veins. Exploration, Injection, Critique").
Masaki, M. et al., "The destructive effects of sclerosant ethanolamine oleate on mammalian vessel endothelium," *Gastroenterologia Japanica*, vol. 25, No. 1, pp. 230-235, Feb. 1990.
Material Safety Data Sheet for polydocanol, 2009.
Mathiesen, F.R., "Subclinical Deep Venous Damage After Sclerosing Injection Demonstrated by Phlebography," *Acta Chirurgica Scandinavica*, vol. 118, No. 2, pp. 155-166, 1959.
Mathiesen, F.R., "Behandlung of Varicer—Retrograd injection eller kommunikantre-sektion," *Nordisk Medicin*, vol. 64, No. 48, pp. 1525-1529, 1960 (Eng. Translation—"Treatment of Varicose Veins—Retrograde Injection or Communicant Resection").

Maurer, W., "Ist die Verodungstherapie bei Varikos in der Praxis zu emfehlen," *Therapie der Gegenwart*, Issue 5, pp. 242-245, May 1961 (Eng. Translation—"Is the sclerosing therapy in the case of varicosis advisable in practice?").
May, R., "Schaden und Gefahren bei der Varizenbehandlung," *Münchener Medizinische Wochenschrift*, No. 1, pp. 13-16, Jan. 1956 (Eng. Translation—"Impairments and Risks of the Treatment of Varicose Veins").
Mayer, G., Die Behandlung des Krampfaderleidens vom Standpunkt der Verodungstherapie, insbesondere unter Verwendung von Varicophtin, *Münchener Medizinische Wochenschrift*, vol. 16, No. 20, cols. 1037-1039, Jan. 1952 (Eng. Translation—"The Treatment of Varicose Veins from the point of View of Sclerotherapy, in particularly on the Basis of Varicophtine".
Mayer, H. et al., "Zur Atiologie und Behandlung der Varizen der unteren Extremitat," *Chirurgische Praxis*, pp. 521-528, 1957 (Eng. Translation—"Angiology: The Aetiology and Treatment of Varicosities of the Lower Extremity").
Medelman, J.P., "Results of Surgical Treatment of Varicose Veins," *The Journal of the American Medical Association*, vol. 178, No. 8, pp. 906-911, Nov. 25, 1961.
Meissner, M., "Pelvic Veins and Vascular Malformation," *American College of Phlebology*, 22nd Annual Meeting, Marco Island, FL. Nov. 6-9, 2008.
*Meyer's Encyclopedia*, 5th Edition, regarding foam, vol. 15, pp. 386, 1895.
Min, R.J.; "Transcatheter Duplex Ultrasound Guided Sclerotherapy," Abstracts from the 13th Annual Congress of the *American College of Phlebology*, Nov. 10-13, 1999.
Miserey, G. et al., "Sclerose Sous Echographie Dans Certaines Zones a Risques," *Phlebologie*, vol. 44, No. 1, pp. 85-96, 1991.
Monfreux, A., "Traitment Sclerosant des Troncs Sapheniens et leurs Collaterales de Gros Calibre par la Methode MUS," *Phlebologie*, 1997, 50, No. 3, 351-353 (Eng. Translation—"Sclerosant Treatment of Saphenous Trunks and Their Large Calibre Collaterals by the MUS Method").
Moore, R.M. et al., "Injections of Air and Carbon Dioxide into a Pulmonary Vein," *Annals of Surgery*, vol. 112, pp. 212-218, 1940.
Morrison, N., "Foam Safety Studies," *American College of Phlebology*, 22nd Annual Meeting, Marco Island, FL, Nov. 6-9, 2008.
Morrison, N., "Strategies for Preventing the Big, Bad Complications," *American College of Phlebology*, 22nd Annual Meeting, Marco Island, FL, Nov. 6-9, 2008.
Morsiani, E. et al., "Effect of Intravenous and Intreperivenous Injections of Sclerosants (Sodium Tetradecyl Sulfate and Hydroxy Polyethoxy Dodecan) on the Rat Femoral Vein," *Research in Experimental Medicine*, vol. 187, pp. 439-449, 1987.
Moszkowiez, L., "Behandlung der Krampfadern mit Zuckerinjektionen kombiniert mit Veneligatur," *Zentralblatt fur Chirurgie*, No. 28, pp. 1731-1736, 1927 (Eng. Translation—"Treatment of Varicose Veins with Sugar Injections, combined with vein ligation").
Muller, R., "Die ambulante Phlebektomie," *Therapeutische Umschau*, vol. 49, No. 7, pp. 447-450, 1992 (Eng. Translation—"The Ambulatory Phlebectomy").
Myers, H.L., "Injection Therapy for Varicose Veins," *The Journal of Family Practice*, vol. 3, No. 5, pp. 531-534, 1976.
Neuhardt, D.L, et al., "Emboli Detection in the MCA Concurrent With Treatment of LE Superficial Venous Insufficiency with Foam Sclerotherapy," *American College of Phlebology*, 22nd Annual Meeting, Marco Island, FL, Nov. 6-9, 2008.
Ochsner, A. et al., "Comparative Value of Intravenous Sclerosing Substances," *Archives of Surgery*, vol. 29, No. 3, pp. 397-416, Sep. 1934.
Oden, H.G., Lassen sich in der Behandlung von Krampfadern and Ulcus cruris die Erfolge verbessern,' *Münchener, Medizinische Wochenschrift*, vol. 22, No. 8, pp. 364, Jan. 1952 (Eng. Translation—"Can the Results of the Treatment of Varicose Vains and Ulcus Cruris be Improved?").
Olivier, C.I. et al., "Les Reinterventions pour Varice Essentielles des Membres Inferieurs," *La Presse Medicale*, vol. 74, No. 26, pp. 1355-1360, May 25, 1966 (Eng. Translation—"Reinterventions Performed on Primary Varicose Veins of the Lower Limbs").

(56) References Cited

OTHER PUBLICATIONS

Olivier, C., "Traitement chirurgical des ulceres trophiques des membres inferieurs," *Journal de Chirurgie*, vol. 78, No. 2, pp. 157-174, Oct. 1959 (Eng. Translation—"Surgical Treatment of Trophic Ulcers of the Inferior Members").

Oppenheimer, M.J. et al., "In Vivo Visualization of Intracardiac Structures with Gaseous Carbon Dioxide—Cardiovascular-Respiratory Effects and Associated Changes in Blood Chemistry," *American Journal of Physiology*, vol. 186, pp. 325-334, Jul.-Sep. 1956.

Orbach, E., "Leg Ulcers of Vascular Origin and Their Therapy," *American Journal of Surgery*, vol. LXXXI, No. 5, pp. 568-572, May 1951.

Orbach, E.J. et al., "Investigation of the Different Injection Techniques in the Sclerotherapy of Varicose Veins by Minidose and Differential Pressure Phlebography," *VASA*, vol. 4, No. 2, pp. 175-183, 1975.

Orbach, E.J. et al., "The Thrombogenic Property of Foam of a Synthetic Anionic Detergent (Sodium Tetradecyl Sulfate N.N.R), Thrombogenic Property of a Detergent," *Angiology—The Journal of Vascular Diseases*, vol. 1, No. 3, pp. 237-243, 1950.

Orbach, E.J., "A Unified Approach to the Therapy of Varicosities," *Angiology*, vol. 15, No. 12, pp. 558-560, Dec. 1964.

Orbach, E.J., "Allergenic Tissue Reaction of Catgut, an Aid for the Obliteration of Varicose Veins," *The Journal of the International College of Surgeons*, vol. XXII, No. 6, pp. 707-710, Dec. 1954.

Orbach, E.J., "Beitrag zur Behandlung von Teleangiektasien," Zentralblatt für Phlebologie, Heft 1, Band 3, pp. 4-7, Feb. 15, 1964 (Eng. Translation—"Article on Treatment of Teleangiectasias").

Orbach, E.J., "Contributions to the Therapy of the Varicose Complex," *Journal of the International College of Surgeons*, pp. 765-771, Jun. 1950.

Orbach, E.J., "Controversies and Realities of Therapy for Varicosis," *International Surgery*, vol. 62, No. 3, pp. 149-151, Mar. 1977.

Orbach, E.J., "Has Injection Treatment of Varicose Veins Become Obsolete?," *The Journal of American Medical Association*, vol. 166., No. 16, pp. 1964-1966, Apr. 1958.

Orbach, E.J., "Hazards of Sclerotherapy of Varicose Veins—their prevention and treatment of complications," *VASA*, vol. 8, No. 2, pp. 170-173, 1979.

Orbach, E.J., "Misconceptions and Pitfalls in Sclerosing Therapy of Varicose Veins," *Angiology—The Journal of Vascular Diseases*, vol. 14, No. 11, pp. 552-555, Nov. 1963.

Orbach, E.J., "Reappraisal of the Sclerotherapy of Varicose Veins," *Angiology—The Journal of Vascular Diseases*, vol. 8, No. 6, pp. 520-527, Dec. 1957.

Orbach, E.J., "The importance of removal of postinjection coagula during the course of sclerotherapy of varicose veins," *VASA*, vol. 3, No. 4, pp. 475-477, 1974.

Orbach, E.J., "The Place of Injection Therapy in the Treatment of Venous Disorders of the Lower Extremity—with Comments on its Technique," vol. 17, No. 1, pp. 18-23, 1966 (Presented at the Annual Meeting of the International College of Angiology, London, Jul. 1965).

Orbach, E.J., "Varicose Veins," *Medical Trial Technique Quarterly*, vol. XIV, No. 4, pp. 27-38, Jun. 1968.

Orbach;E.J., "Sclerotherapy of Varicose Veins—Utilization of an Intravenous Air Block," *American Journal of Surgery*, vol. LXVI, No. 3, pp. 362-366; Dec. 1944.

Ouvry, P. et al., "L. Aétoxisclérol: Premieres Impressions," *Phlébologie*, vol. 31, No. 2, pp. 75-77, 1978 (Eng. Translation—"Aétoxisclérol: First Impressions").

Ouvry, P. et al., "Le Traitement Sclérosant des Télangiectasies des Membres Inférieurs," *Phlébologie*, vol. 32, No. 4, pp. 365-370, 1979 (Eng. Translation—"Sclerosant Treatment of Telangiectasias of the Lower Limbs").

Ouvry, P., et al., "Le Traitment Sclerosant des Telangiectasies des Membres Inferieurs," *Phlébologie*, vol. 35, No. 1, pp. 349-359, 1982 (Eng. Translation—"The Sclerotherapy of Telangiectasia").

Ouvry, P. et al., "La Sclerotherapie des Perforantes," *Phlébologie*, vol. 40, No. 3, pp. 633-641, 1987 (Eng. Translation—"Sclerotherapy of Perforating Veins").

Ouvry, P.A., "Telangiectasia and Sclerotherapy," *J. Dermatol. Surg. Oncol.* vol. 15, No. 2, pp. 177-181, Feb. 1989.

Pfosi, H., Zur sklerosierenden Behandlung der Varizen, *Schweizerische Rundschau für Medizin—Revue Suisse de Medecine*, 54$^{th}$ year of Edition, No. 29, pp. 868-871, Jul. 22, 1965 (eg. Translation—"On the Sclerosing Treatment of Varicose Veins").

Pittalugap, P., "The Complex Case," *American College of Phlebology*, 22$^{nd}$ Annual Meeting, Marco Island, FL, Nov. 6-9, 2008.

Piulachs, P. et al., "Considerations Pathogeniques sur les Varices de la Grossesse," Lyon Chirurigical, *Bulletin officiel de la Societe de Chriurgie de Lyon*, vol. 47, No. 3, pp. 263-278, Apr. 1952 (Eng. Translation—"Pathogenic Considerations on Varicose Veins Developed in Pregnancy").

Piulachs, P. et al., "Pathogenic Study of Varicose Veins," *Angiology*, The Journal of Vascular Diseases, vol. 4, No. 1, pp. 59-100, Feb. 1953.

Postma, G.J., "Ethanolamine-oleaat injectie: therapeutische en farmaceutische aspecten," *Ziekenhuis Farmacie*, No. 3, pp. 84-91, Sep. 1992 (Eng. Translation—"Ethanolamine Oleate Injection: Therapeutic and Pharmaceutical Aspects").

Proebstle, T., "One and Two Years Follow-Up of Radiofrequency Segmental Thermal Ablation (RSTA) of Great Saphenous Veins," *American College of Phlebology*, 22$^{nd}$ Annual Meeting, Marco Island, FL, Nov. 6-9, 2008.

Rabe, E. et al.; Leitlinien zur Verodungsbehandlung der Varikose,Leitlinien der DGP, *Phlebologie*, pp. 154-158; 2001 (eng. Translation—"Guidelines to the Sclerosing Treatment of Varicose Veins").

Rabe, E., "Polidocanol, Sodium Tetradecyl Sulfate and Placebo for Sclerotherapy of C1-Varicose Veins," *American College of Phlebology* 22$^{nd}$ Annual Meeting, Marco Island, FL, Nov. 6-9, 2008.

Ramstad, K.R. et al., "Operativ Behandling av Varicer," Tidsskrift for Den Norske Laegeforening, No. 10, pp. 623-625, May 1959 (Eng. Translation—"Operative Treatment of Varicose Veins—Follow-up of Patients treated with ligature/injection and "stripping" respectively").

Rappert, E., "Forschund and Praxis: Was leistet die chirurgische Therapie der Varizen und des Ulcus cruris," Die Medizinische, No. 22. pp. 907-914, May 1958 (Eng. Translation—The achievements of surgical therapy of varicose veins and leg ulcers?).

Rappert, E., "Die Therapie des Ulcus cruris varicosum," Wiener Medizinische Wochenschrift, vol. 106, No. 48, pp. 999-1000, Dec. 1, 1956 (Eng. Translation—"The Therapy of Varicose Crural Ulcers").

Rappert, E., "Variaenbehandlung nach Phlebitis und Thrombose," Wiener Medizinische Wochenschrift, No. 4, pp. 100-101, 1957 (Eng. Translation—"The treatment of varicose veins following a phlebitis and thrombosis").

Rathbun, S., "Venous Thromboembolism: The Problem," *American College of Phlebology*, 22$^{nd}$ Annual Meeting, Marco Island, FL, Nov. 6-9, 2008.

Rauhs, R., "Die Sklerotherapie, ihre Indikationen und Behandlungserfolge," Klinische Medizin, Issue 1, pp. 5-12, Jan. 1961 (Eng. Translation—"Sclerotherapy, its indications and treatment successes").

Ree, A., "Varicebehandling Med Scum av Etamolin (NYCO)," , Dansk Lægeforening, No. 12-15, pp. 452-453, Jun. 1955 (Eng. Translation—"Varicose Vein Treatment with Foam of Etamolin (NYCO)").

Ree, A.; "The Treatment of Varicose Veins with Etamolin Foam"; Acta Dermato-Venereologica; vol. 39, pp. 428-432; 1959.

Reiner, L., "The Activity of Anionic Surface Active Compounds in Producing Vascular Obliteration," Surface Active Sclerosing Agents, Proceedings of the Society for Experimental Biology and Medicine, vol. 62, pp. 49-54, May-Jun. 1946.

Reinharez, D., "Pratique de la Sclerose des Perforantes," Phlébologie, vol. 31, No. 2, pp. 69-74, 1978 (Eng. Translation—"Perforating Vein Sclerosis Technique").

Robertson, C.S., "A Study of the Local Toxicity of Agents Used for Variceal Injection Sclerotherapy," HPB Surgery, vol. 1, pp. 149-154, 1989.

(56) References Cited

OTHER PUBLICATIONS

Rogge, H., "Gefahren der Varizen-Verodung bel Rezidiven," Deutsche Medizinische Wochenschrift, No. 9, p. 301, 1950 (Eng. Translation—"On the dangers of sclerosing recurring varicose veins").

Rompp, H.; "Varsyl"; Chemie Lexikon, Vierte Vollig Neu Bearbeitete Auflage; p. 4649; 1958.

Rowden-Foote; R., "Varicose Veins Hemorrhoids and Other Conditions—Their Treatment by Injection"; London, H.K. Lewis & Co. Ltd.; pp. 13-45, 106-119; 1944.

Rush, J., "Neurological and Visual Symptoms Following Treatment of the Saphenous Veins with Two Formulations of Polidocanol Endovenous Microfoam," American College of Phlebology, 22nd Annual Meeting, Marco Island, FL, Nov. 6-9, 2008.

Sadoun, S., "Sclerosing Foam: Material and Methods," in Foam Sclerotherapy State of the Art, ed. J.P. Henriet, Editions Phlébologiques Francaises, pp. 25-32, 2002.

Salamon, Z., "Leki Obliterujace ich Toksycznosc I sposob Dzialania," Wiadomosci Lekarskie, vol. 26, No. 19, pp. 1819-1822, 1973 (Eng. Translation—"Sclerosing Agents—Toxicity and Mechanism of Action").

Santler, R., "Zur Verodungstherapie der Varizen," Weiner Klinische Wochenschrift, Issue 24, No. 76, pp. 431-434, Jun. 12, 1964 (Eng. Translation—"Sclerosing Therapy of Varicose Veins").

Savonuzzi, G. et al., "Un metodo di terapia delle affezioni varicose dell'arto inferiore con associazione di sostane sclerosanti ed anticoagulanti," Minerva Medica, vol. XLVIII, No. 24, pp. 1124-1126, Mar. 24, 1957 (Eng. Translation—"A Therapeutic Method that Combines Sclerosing Agents and Anticoagulants for varicose diseases of the lower limb").

Schadeck, M. et al., "Echotomographie de la Sclerose," Phlebologie, vol. 44, No. 1, pp. 111-130, 1991.

Schadeck, M., "La Sclerotherapie Chez L'enfant," Phlébologie, vol. 45, No. 4, pp. 509-512, 1992 (Eng. Translation—"Sclerotherapy in the Child").

Schadeck, M.; "Duplex-kontrollierte Sklerosierungsbehandlung der Vena saphena magna," Phlebol; vol. 25, pp. 78-82; 1996 (Eng. Translation—"Duplex Controlled Sclerosing Treatment of the Great Saphenous Vein").

Schadeck, M.; Echo-sclerose de la Grand Saphene, Phlébologie; vol. 46, No. 4, pp. 673-682, 1993 (Eng. Translation—"Ultrasound-controlled Sclerotherapy of the Great Saphenous Veins"; .

Schliephake, D., "A New Standardized Digital Imaging System to Document Treatment Success After Sclerotherapy of C1 Varicose Veins Applied in a Double-Blind, Randomized, Controlled Clinical Trial (EASI Study)," American College of Phlebology, 22nd Annual Meeting, Marco Island, FL, Nov. 6-9, 2008.

Schmier, A., "Clinical Comparison of Sclerosing Solutions in Injection Treatment of Varicose Veins, Delayed Slough: Recurrence of Varices," The American Journal of Surgery, vol. XXXV, No. 1, pp. 389-397, Apr. 1937.

Schneider, H.O., Varizenbehandlung mit einem modernen Verodungsmittel, Zeitschrift für Haut und Geschelchts-krankheiten, Band XXXIII, Heft No. 5, pp. 163-166, Sep. 1962 (Eng. Translation—"Varix Treatment with a Modern Sclerosing Agent").

Schneider, W. et al., "Zur Histologie der Varicenverodung am Menschen mit neueren Verodungsmitteln," Klinische und Experimentelle Dermatologie, vol. 220, pp. 234-249, 1964 (Eng. Translation—"On the histology of the Varicose Injection Treatment in People with new Injection Treatment Agents,".

Schorcher, F., "Originalaufsatze und Vortrage," Münchener Medizinische Wochenschrift, No. 41, pp. 1354-1358, Oct. 1955 (Eng. Translation—"For the Practice Varicose Veins and Deep Chronic Crural Thrombosis").

Schul, M., et al., "Compression Therapy vs. Sclerotherapy for Isolated Refluxing Reticular Veins and Telangiectasia: 12 Month Results of a Randomized Trial," American College of Phlebology, 22nd Annual Meeting, Marco Island, FL, Nov. 6-9, 2008.

Schul, M., et al., "Insurance Denials," American College of Phlebology, 22nd Annual Meeting, Marco Island, FL, Nov. 6-9, 2008.

Scneider, W., "Zur nicht-operativen Varizenverodung," Die Medizinische Welt, vol. 3, No. 5, pp. 225-227, Jan. 1961 (Eng. Translation—"Regarding non-operative varicosclerosation").

Seeger, J. et al., "Carbon Dioxide Gas as an Arterial Contrast Agent," Annals of Surgery, vol. 217, No. 6, p. 688-698, 1993.

Shafi, Z.B. et al., "Factors Affecting High Shear Preparation of Albumin Microspheres," Pharmaceutical Sciences Research Group, p. 144P, 1990.

Sica, M., "Ultrasound Appearance of Sclerosing Foam," in Foam Sclerotherapy State of the Art, ed. J.P. Henriet, Editions Phlébologiques Francaises, pp. 85-88, 2002.

Sicard, P., "Traitment Sclerosant des Varices des Membres Inferieurs," Therapeutique, vol. 36, No. 2, pp. 127-129, Feb. 1960(Eng. Translation—"Sclerosing Treatment of Varicose Veins of the Lower Limbs").

Sigg, K., "Zur Behandlung der Varizen und ihrer Komplikationen," Dermatologica, vol. 100, p. 317, 1950 (Eng. Translation—"Regarding treatment of varicose veins and their complications").

Sigg, K., "Neuere Gesichtspunkte zur Technik der Varizenbehandlung," Therapeutishce Umschau, vol. 6, pp. 127-134, Dec. 1949 (Eng. Translation—"Newer Points of View on the Tecnique of Varicose Vein Treatment").

Sigg, K. et al., "Neue Varizenverodungs-mittel," Munchener Medizinische Wochenschrift, Issue 1, Mar. 1961 (Eng. Translation—"New Sclerosing Substances for Varicose Veins").

Sigg, K. et al., "Thromboseprophylaxe wahrend der Schwangerschaft," Die Medizinische, No. 12, pp. 421-423, Jan. 1957 (Eng. Translation—"Prophylaxis of Thrombosis during Gravidity").

Sigg, K. et al., "Varicenbehandlung durch Sklerosierung," Langenbacks Arch. Chir., vol. 347, pp. 231-234, 1978 (Eng. Translation—"Treating varices with Sclerotherapy").

Sigg, K., "Physiologischer Wert und nosologische Bedeutung der Manu-volumetrie," Munchener Medizinische Wochenschrift, vol. 99, No. 17, pp. 581, 610-613, Apr. 1957 (Eng. Translation—"A Good Prophylaxis of Thrombosis during Pregnancy, delivery and childbed as well as for Operations can Prevent the Thrombo-Embolism").

Sigg, K., "La Profilassi e la terapia delle malattie venose degli arti inferiori mediante la compressione con fasciature e con calze elastiche," Minerva Ginecologica, vol. 16, No. 19, pp. 817-823, Oct. 15, 1964 (Eng. Translation—"The prophylaxis and therapy of venous disease in the lower limbs by means of compression with bandages and elastic stockings").

Sigg, K., "New Approaches to the Treatment of Thrombosis," Angiology—The Journal of Vascular Diseases, vol. 8, No. 1, pp. 44-59, Feb. 1957.

Sigg, K., "Varicenverodung, Durchfuhrung und Resultate," Der Chirurg, vol. II, No. 40, pp. 487-491, 1969 (Eng. Translation—"Phlebosclerosation: experience and results").

Sigg, K., Wiener Medizinische Wochen-schrift, No. 10, pp. 206-213, Mar. 1958 (Eng. Translation—"Prevention and Treatment of Thromboembolic Complications").

Sigg, K., et al., Zur Diskussion gestellt—Open for Discussion, VASA, vol. 4, No. 1, pp. 73-78, 1975 (Eng. Translation—"Quick Treatment—a modified Method of Sclerotherapy of Varicose Veins").

Sigg, K., "Sclerotherapy in the Treatment of Varicose Veins," Der Internist, pp. 388-398, 1967.

Sigg, K., "Technische Einzelheiten zur Varizeninjekton," Med. Klin., vol. 67, No. 27/28, pp. 955-959, 1972 (Eng. Translation—"Technical Details about Injecting Varices").

Sigg, K., "Die ambulante Behandlung der Phlebitis," Schwiezerische Medizinische Wochenschrift, vol. 80, No. 2, pp. 33-39, Jan. 1950 (Eng. Translation—"The Ambulatory Treatment of Phlebitis").

Sigg, K., "Die Schaumgummi-Kompressionder Phlebitis sowie der phlebitischen und varikosen Komplikationen," Die Medizinische, No. 27-28, pp. 910-915, Jul. 1952 (Eng. Translation—"The Foamed Rubber Compression for Phlebitis and for Phlebitic and Varicose Complications").

Sigg, K., Die Behandlung des Ulcus cruris, Die Medizinische, No. 17, pp. 646-648, 1955 (Eng. Translation—"The Treatment of Leg Ulcers").

Sigg, K., "The Treatment of Varicosities and Accompanying Complications," Angiology—The Journal of Vascular Diseases, vol. 3, No. 5, pp. 355-379, Oct. 1952.

(56) References Cited

OTHER PUBLICATIONS

Sigg, K., "Therapeutische Probleme," *Schweizerische Medizinische Wochen-schrift*, 65th year of the edition, No. 11, pp. 261-262, Mar. 12, 1955 (Eng. Translation—"Therapeutic Issues—On the Treatment of Vein Thrombosis with Butazolidin").

Sigg, K., "Traitment des thromboses superficielles et profondes et l'application de Butazolidine," *Gynaecologia, Supplementum*, vol. 144, pp. 19-23, Jul. 1956 (Eng. Translation—"Treatment of Superficial and Deep Thrombosis and the Application of Butazolidine").

Sigg, K., "Behandlung der Varizen, des Ulcus cruris und der Thrombose," *Weiner Medizinische Wochenschrift*, No. 6, Feb. 11, 1961 (Eng. Translation—"Treatment of Varices, varicose ulcer and thrombosis").

Sigg, K., *Dermatologica*, vol. 129, No. 2, pp. 111-117, 1964 (Eng. Translation—"Treatment of Varicose Veins in 2-5 days").

Sigg, K., "Die Varizentherapie," *Deutsche Medizinische Wochenschrift*, No. 15, pp. 665-666, Apr. 9, 1965 (Eng. Translation—"Varicose Vein Therapy").

Sigg, K., "Krampfadern und tiefe chronische Beinvenenthrombose," *Münchener Medizinische Wochenschrift*, vol. 98, No. 8, pp. 260-263, Feb. 1956 (Eng. Translation—"Varicose Veins and Deep Seated Chronic Leg Vein Thrombosis").

Sigg, K., "Varikosis und Thrombose bei Schwangerschaft, Geburt und Wochenbett," *Zentralblatt für Gynäkologie*, No. 8, pp. 254-259, Feb. 23, 1963 (Eng. Translation—"Varicosis and Thrombosis during Pregnancy, birth and in childbed").

Singh, I., "Life Without Breathing II," *Arch. Int. Pharmacodyn.*, vol. CXXXVII, No. 3-4, pp. 318-330, 1962.

Slutsky, E., "Sclerotherapy Complica-tions Matting, Staining and Lack of Improvements," *American College of Phlebology*, 22nd Annual Meeting, Marco Island, FL, Nov. 6-9, 2008.

Smith, P.C, "Foam Sclerotherapy in Treatment of Varicose Veins: Results from Europe," Invited Presentation at Pacific Vascular Symposium, Kona, Nov. 2002 (Abstract).

Steffey, E. et al., "Nitrous Oxide Intensifies the Pulmonary Arterial Pressure Response to Venous Injection of Carbon Dioxide in the Dog," *Anesthesiology*, vol. 52: pp. 52-55, 1980.

Steinacher, J. et al., "Weg und Verweildauer eines Kontrastmittels im oberflachen Venensystem unter Bedingungen der Varicenverodung. Ein Studie zur Technik der Varicenverodung," *Zsch. Haut-Geschl*, vol. 43, No. 9, pp. 369-374, 1968 (Eng. Translation—"Path and Retention Time of a Contrast Medium in the Superficial Venous System under the Conditions of Varix Obliteration. A Study on the method of varix obliteration").

Steinberg, M.H., "Evaluation of Sotradecol in Sclerotherapy of Varicose Veins," *Angiology—The Journal of Vascular Diseases*, vol. 6, No. 6, pp. 519-532, Dec. 1955.

Stemmer, B. et al., "Ercevit un double impact thérapeutique," *Phlebologie*, vol. 22, No. 2, pp. 151-172, Apr.-Jun. 1969.

Stemmer, B., "Comparison of Common Sclerosing Techniques," *Zentralblatt für Phlebologie*, vol. 3, pp. 170-176, 1970.

Stern, W., "Varicose Veins," The Medical Journal of Australia, vol. II, No. 18, pp. 849-852, Oct. 29, 1960.

Stoughton, J., et al., "Basic Sclerotherapy," *American College of Phlebology*, 22nd Annual Meeting, Marco Island, FL, Nov. 6-9, 2008.

Syllabus & Scientific Abstracts of the UIP World Congress Chapter Meeting, San Diego, California, Aug. 27-31, 2003.

Tessari, L., "Nouvelle Technique d'Obtention de la Sclero-mousse," *Phlebologie*, vol. 53, No. 1, p. 129, 2000 (Eng. Translation—"New Technique for Obtaining Sclero-Foam").

Tessari, L., et al., "Preliminary Experience with a new Sclerosing Foam in the Treatment of Varicose Veins," *Dermatol. Surg.*, 2001, 27, 58-60.

Tessari, L., "The 'Tourbillon Turbulence' Tessari's method with the three-way tap device," in Foam Sclerotherapy State of the Art, ed. J.P. Henriet, *Editions Phlébologique Francais*, pp. 51-55, 2002.

Thibault, P.K. et al., "Recurrent Varicose Veins," *Phlebology*, vol. 18, pp. 895-900, 1992.

Tournay, R., "Indikationen der alleinigen Verodungsbehandlung oder der zweizeitigen Kombinationsbehandlung Chirurgie-Verodung bei Krampfadern," *Zentralblatt für Phlebologie*, vol. 4, No. 1, pp. 133-142, Feb. 1965 (Eng. Translation—"Indication of the Exclusive Sclerotherapy or the Consecutive Combination Therapy Surgery-Sclerotization of Varicose Veins").

Tunick, I.S. et al., "Sodium Morrhuate as a Sclerosing Agent in the Treatment of Varicose Veins," Annals of Surgery, vol. XCV, pp. 734-737, 1932.

Tunnicliffe, F.W. et al., "The Intravenous Injection of Oxygen Gas as a Therapeutic Measure," *Lancet*, vol. II, pp. 321-323, 1916.

Vacheron, J and P, "Les varices essentielles de membres inférieurs Traitement sclérosant par ruissellemtn," *Archives de Maladies du Coeur*, 7th Year, No. 12, pp. 1033-1038, Dec. 1954 (Eng. Translation—"Essential Varicose Veins on Lower Limbs: Sclerosant Treatment by Streaming").

Varshavskii, B.Y, "Mechanism of changes in renal activity following intravenous oxygen," *Sechenov Physiological Journal of the USSR*, vol. 53, No. 2, pp. 173-177, 1967.

Vasdekis, S.N. et al., "Evaluation of non-invasive and invasive methods in the assessment of short saphenous vein termination," *Br. J. Surg.*, vol. 76, No. 9, pp. 929-932, Sep. 1989.

Vin, F., "Echo-sclerotherapie de la veine saphene externe," *Phlébologie*, vol. 44, No. 1, pp. 79-84, 1991 (Eng. Translation—"Echo-Sclerotherapy of the Small Saphenous Vein").

Voss, F., Spezielle Praktiken bei der Sklerosierungsbehandlung venoser Beinleiden, *Zeitschrift fër Haut-und Geschlechts-Krankheiten*, vol. XXVII, No. 9, pp. 304-306, 1960 (Eng. Translation—"Special Methods in the Sclerotherapy of Venous Leg Maladies").

Wakefield, T., "Diagnosis and Management of PE," *American College of Phlebology*, 22nd Annual Meeting, Marco Island, FL, Nov. 6-9, 2008.

Wakefield, T., "New Anticoagulants, (Total US 2002 VTE Events)" *American College of Phlebology*, 22nd Annual Meeting, Marco Island, FL, Nov. 6-9, 2008.

Wefers, H. et al., Ergebnisse der Injektionsbehandlung bei hochgradien Varizenbildungen, *Zentralblatt für Chirurgie*, Issue No. 43, pp. 1825-1828, 1952 (Eng. Translation—"Results of Injection Treatment with Regard to Extreme Varication").

Weindorf, N. et al., "Controle du Traitment par Sclerose des Varices," *Phlébologie*, vol. 43, No. 4, pp. 681-687, 1990 (Eng. Translation—"Control of Sclerosis—Treatment for Varicose Veins").

Wesener, G., "Forum des Praktikers," *Berufs-Dermatosen*, vol. 17, No. 5, pp. 273-281, Oct. 1969 (Eng. Translation—"Morphology and new therapies for starburst varicosis and essential telangiectasia").

Westhues, H. et al., "Der varicose Symptomenkomplex," *Medizinische Klinik*, No. 16, pp. 657-660, 1957 (Eng. Translation—"The Varicose Symptom Complex").

Weston, R.E. et al., "The Influence of Denitrogenation on the Response of Anesthetized Dogs to Intravenously Injected Oxygen," *The Journal of Clinical Investigation*, vol. 26, pp. 837-848, Sep. 1947.

Wiedmann, A., "Der varicose Symptomenkomplex Bericht uber die Literatur den Jahren 1955-1960, Teil I, Varicen," *Der Hautarzt*, vol. 12, No. 9, pp. 433-438, Oct. 1961 (Eng. Translation—"The Varicose Symptom Complex Report on the Literature from the years 1955-1960, Part 1, Varices").

Willenegger, H. et al., "Versuch zur Durchfuhrung einer Thromboembolie- prophylaxe ohne Antikoagulatien," *Schweizerische Medizinische Wochenschrift—Journal Suisse de Medecine*, vol. 87, Supplement for No. 24, pp. 739-748, 1957 (Eng. Translation—"Attempt at carrying out Thromboembolism Propylaxis without Anticoagulants").

Wollmann, J., 60 Jahre Sklerosier-ungsschaum, *Phlebologie*, vol. 33 p. 63-70, 2004 (Eng. Translation—"60 years of Sclerosing Foam").

Wollmann, J.G.R., "The History of Sclerosing Foams," *Dermatol. Surg.*, vol. 30, pp. 694-703, 2004.

Wollmann, J.C. et al.; "Evaluation of the Tests, K25," *Kreussler Pharma*; pp. 17-28, Jan. 2003.

Wright, D. et al., "A Single Center Pilot Study of Polidocanol Endovenous Microfoam (PEM) Treatment to Evaluate Presence and

(56) References Cited

OTHER PUBLICATIONS

Durability of Gas Emboli Using Echocardiography," *American College of Phlebology*, 22nd Annual Meeting, Marco Island, FL, Nov. 6-9, 2008.
Wright, D., Presentation, "The Varisolve® Trial Will Foam Make EVLA and RFA obsolete?," 2008 (38 pages).
Zingg, R., "Experimental tests with the new sclerosing agent 'Geigy'," pp. 1-9, 1948 (Eng. Translation).
Office Action dated Nov. 14, 2008 for U.S. Appl. No. 10/536,862.
Co-pending U.S. Appl. No. 10/536,862, filed May 27, 2005.
Co-pending U.S. Appl. No. 10/522,529, filed Aug. 11, 2006.
Office Action dated May 6, 2009 for U.S. Appl. No. 10/522,529.
Office Action dated Dec. 15, 2009 for U.S. Appl. No. 10/522,529.
Co-pending U.S. Appl. No. 11/128,265, filed May 13, 2005.
Office Action dated Jan. 9, 2008, in co-pending U.S. Appl. No. 11/128,265.
Office Action dated Jun. 12, 2008, in co-pending U.S. Appl. No. 11/128,265.
Office Action dated Dec. 19, 2008, in co-pending U.S. Appl. No. 11/128,265.
Office Action dated Jun. 23, 2009, in co-pending U.S. Appl. No. 11/128,265.
Co-pending U.S. Appl. No. 10/522,525, filed Nov. 1, 2005.
Office Action dated Dec. 14, 2009, in co-pending U.S. Appl. No. 10/522,525.
Office Action dated Apr. 15, 2009, in co-pending U.S. Appl. No. 10/522,525.
Office Action dated Aug. 6, 2008, in co-pending U.S. Appl. No. 10/522,525.
Office Action dated Feb. 20, 2008, in co-pending U.S. Appl. No. 10/522,525.
Office Action dated Jul. 25, 2007 in co-pending U.S. Appl. No. 10/522,525.
Co-pending U.S. Appl. No. 10/522,528, filed Apr. 27, 2006.
Office Action dated Jun. 5, 2009 in co-pending U.S. Appl. No. 10/522,528.
Office Action dated Oct. 16, 2008 in co-pending U.S. Appl. No. 10/522,528.
Co-pending U.S. Appl. No. 10/522,527, filed Oct. 10, 2006.
Office Action dated Apr. 28, 2009, in co-pending U.S. Appl. No. 10/522,527.
Office Action dated Aug. 6, 2008, in co-pending U.S. Appl. No. 10/522,527.
Office Action dated Nov. 1, 2007, in co-pending U.S. Appl. No. 10/522,527.
Co-pending U.S. Appl. No. 11/914,192, filed May 30, 2008.
Notice of Publication of Application dated May 14, 2009, in co-pending U.S. Appl. No. 11/914,192.
Co-pending U.S. Appl. No. 10/890,267, filed Jul. 14, 2004.
Co-pending U.S. Appl. No. 11/914,190, filed May 30, 2008.
Co-pending U.S. Appl. No. 11/225,860, filed Sep. 30, 2009.
Co-pending U.S. Appl. No. 11/171,293, filed Jul. 1, 2005.
Co-pending U.S. Appl. No. 10/432,328, filed Apr. 2, 2004.
Communication from the Examining Division of the European Patent Office in EP04798564, dated Apr. 26, 2007.
Reply to Communication from the Examining Division of the European Patent Office in EP04798564, dated Jan. 18, 2008.
Notice of Allowance in U.S. Appl. No. 10/522,527, mailed Jan. 25, 2010.
Notice of Allowance in U.S. Appl. No. 11/225,860, mailed Apr. 30, 2009.
Hobbs, J.T., "Surgery or Sclerotherapy for Varicose Veins," *Lancet*, p. 1149 (1978).
Hobbs, J.T., "The Treatment of Varicose Veins—A Random Trial of injection-Compression Therapy Versus Surgery," *Brit J. Surg.*, vol. 55, No. 10, pp. 777-780, (Oct. 1968).
Hobbs, J.T., "The Treatment of Varicose Veins in Dublin," *Clinical Supplement*, pp. 57-60 (1961).

Hobbs, J.T. Varicose Veins, *ABC of Vascular Diseases*, vol. 303, pp. 707-710 (Sep. 21, 1991).
Wollmann, J.C., "Sclerosant Foams: Stabilities, Physical Properties and Rheological Behavior," *Phlebologie*, pp. 208-217 (Apr. 2010).
Hartke and Mutschler, "Sauerstoff (Oxygen)," DAB 9 Kommentar, vol. 3 pp. 3055-3059 (1986).
Diepenbrock, F., "Phlebocid®" Gehes Codex, Berlin, p. 965 (1960).
Kreussler Pharma, "Video K24 Transcript," (Jan. 28, 2003).
Kreussler Pharma, "Versuchsauswertung" (Jan. 29, 2003).
Eckmann, D.M., "*Microvascular embolization following polidocanol micro foam sclerosant administration*," Dermatol. Surg. vol. 31 pp. 636-643 (Jun. 2005).
Forlee, M.V., "*Stroke after varicose vein foam injection therapy*," J. Vasc. Surg. vol. 43 pp. 162-164 (Jan. 2006).
Eckmann, D.M., "*Regarding 'Stroke after varicose vein foam injection therapy*,'" J. Vasc. Surg. vol. 44 p. 225 (Jul. 2006).
O'Hare, J.L. "The use of foam sclerotherapy for varicose veins: A survey of the members of the Vascular Society of Great Britain and Ireland," Eur. J. Vasc. Endovasc. Surg. vol. 34: 232-35 (2007).
Sebba, F., "*Chapter 5: Colloidal gas aphrons*," Foams & Biliquid Foams—Aphrons pp. 63-78 (1987).
Raven, J.P., "*Dry microfoams: formation and flow in a confined channe*," Eur. Phys. J. B. vol. 51 pp. 137-143 (2006).
Belcaro, G., "*Foam-sclerotherapy, surgery, sclerotherapy, and combined treatment for varicose veinsL A 10-year, prospective, randomized, controlled trial (VEDICO\* Trial)*," Angiology vol. 54 pp. 307-315 (2003).
Hamel-Desnos, C. "*Efficacy of sclerosing foams: summary of the main published clinical trials*," Angeologie vol. 56 pp. 39-44. (2004).
Ganan-Calvo, A.M. "*Coarsening of monodisperse wet microfoams*," Applied Physics Letters vol. pp. 4989-4991 (Jun. 2004).
Breu, F.X., "*Reversible neurologische Komplikationen bei der Schaum-Sklerotherapie*," Phlebologie pp. 115-116 (2006).
Rush, J.E., "*Neurological and visual symptoms following treatment of the great saphenous vein with two formulations of polidocalnol endovenous micro foam*." Phlebology vol. 24 pp. 85-95 (2009).
Sylvoz, N. "*Polidocanol induced cardiotoxicity: a case report and review of the literature*," J. des Maladies Vasculaires vol. 33 pp. 234-238 (2008).
Guex, J., "*Immediate and midterm complications of sclerotherapy: report of a prospective multicenter registry of 12,173 sclerotherapy sessions*," Dermatol. Surg. vol. 31 123-28 (2005).
Simpson, P. "D1 Syringe," (Oct. 13, 2008).
Bruke, V.H., "*Die kombinierte schaumverodung der varizen*," Wiener Medizinische Wochenschrift pp. 111-113. (1954).
Biegeleisen, H., "*Fatty Acid Solutions for the Injection Treatment of Varicose Veins*," Annals of Surgery, vol. CV, pp. 610-615 (1937).
Notice of Abandonment dated Mar. 10, 2011 for U.S. Appl. No. 10/522,529.
Office Action dated Jun. 12, 2008 for U.S. Appl. No. 11/128,265.
Office Action dated Oct. 19, 2008 for U.S. Appl. No. 11/128,265.
Office Action dated Jun. 23, 2009 for U.S. Appl. No. 11/128,265.
Notice of Allowance dated Feb. 7, 2011 for U.S. Appl. No. 11/128,265.
Notice of Allowance dated May 26, 2011 for U.S. Appl. No. 11/128,265.
Issue Notification dated Oct. 12, 2011 for U.S. Appl. No. 11/128,265.
Office Action dated Dec. 14, 2009 for U.S. Appl. No. 10/522,525.
Notice of Abandonment dated Jun. 29, 2010 for U.S. Appl. No. 10/522,525.
Notice of Allowance dated Mar. 9, 2010 for U.S. Appl. No. 10/522,528.
Issue Notification dated Jul. 7, 2010 for U.S. Appl. No. 10/522,528.
Notice of Allowance dated Jan. 25, 2010 for U.S. Appl. No. 10/522,527.
Issue Notification dated May 19, 2010 for U.S. Appl. No. 10/522,527.
Co-pending U.S. Appl. No. 12/765,980, filed Apr. 23, 2010.
Office Action dated Aug. 5, 2010 for U.S. Appl. No. 11/914,190.
Notice of Abandonment dated Feb. 16, 2011 for U.S. Appl. No. 11/914,190.

\* cited by examiner

THERAPEUTIC FOAM

This application is a national stage filing under 35 U.S.C. §371 of International Application No. PCT/GB2006/001754 filed on May 12, 2006. This application claims priority of British Patent Application No. 0509824.9, filed on May 13, 2005 and British Patent Application No. 0517361.2, filed Aug. 24, 2005, all of which are incorporated herein by reference.

The present invention relates to a therapeutic foam e.g. for treatment of varicose veins.

In recent years the use of sclerosing chemicals in the form of foams has become a popular way of treating varicose veins. Foam is injected into the affected vein whilst it progress is monitored using ultrasound scanning. The process causes sclerosis and functional elimination of the vein. Other disorders such as venous malformations may also be treated this way.

Most practitioners make foam extemporaneously using ambient air as the gaseous component. As extensively discussed in copending patent applications nos. PCT/GB04/004824, PCT/GB04/004831, PCT/GB04/004846 and PCT/GB04/004848, the use of air foams is potentially harmful and, in the view of the inventors, is to be avoided. The inventors have followed the key disclosure by the Cabreras in their patent EP0656203B who first proposed a microfoam with oxygen or carbon dioxide as the gas component. Carbon dioxide and oxygen are respectively dissolved blood in or absorbed by haemoglobin, thus making both considerably more attractive than air.

There are other gases which are very soluble, e.g. nitrous oxide. Helium has also been considered since it passes easily across pulmonary gas exchange membranes and hence is exhaled from the body quickly.

The inventors have now surprisingly realised that the gas need not be soluble and need not necessarily be absorbed only by the blood: it is possible to overcome the problem of foam treatment leaving residual gas in the body by using a gas component which dissolves into tissue other than blood, e.g. the vein walls. In this context, they have conceived of the possibility of using a lipid soluble gas, e.g. one or more of the noble gases, as a substantial proportion (greater than 40%) of the gas component of the foam. The higher molecular weight noble gases, especially xenon, are known to dissolve in lipid, e.g. in cell walls. Thus it appears that these gases may be taken up by the body quickly if injected into the venous system, both into the cells of the vein walls and into the blood cells. This dual mode of uptake may give rise to very fast absorption, especially if the gas also has a degree of solubility in water as well. Speed of uptake is critical because if gas is taken up slowly, this may give the opportunity for nitrogen which is already dissolved in the blood to diffuse into the foam, potentially causing enduring bubbles. Again, this is discussed at length in the copending applications mentioned above.

According to the present invention a foam is provided comprising a liquid phase and a gas phase wherein the liquid phase comprises at least one sclerosing agent and the gas phase comprises between 41% and 100% of a gas which is lipid soluble, preferably between 50 and 100%, more preferably between 60 and 100%, still more preferably between 70 and 100%, 80 and 100% or 90 and 100%.

The lipid soluble gas may be argon, krypton or xenon or a mixture of these. The most preferred of these is xenon. Xenon is used as an anaesthetic, and its behaviour in body tissue is well understood: see for example "Xenon Anesthesia": Lynch et al, *Anesthesiology*, v92, No. 3, March 2000. Xenon has the further advantage that it is moderately soluble in water (mole fraction solubility $7.9 \times 10^{-5}$, which is three times as soluble as oxygen).

If the lipid soluble gas does not make up 100% of the gas phase, then it is preferred that the remainder of the gas phase consist essentially of oxygen, carbon dioxide or a mixture of the two.

EXAMPLE

A fume cupboard is filled with greater than 99% pure xenon gas, after placing in the cupboard a small (100 ml) beaker containing 10 ml 1% polidocanol solution, together with a small hand held electric motor with a chuck in which is mounted a small (10 mm diameter) dental brush. The motor is switched on and the speed adjusted to 12,000 r.p.m. The dental brush is then gently inserted into the liquid in the beaker, such that a vortex is formed in the surface of the liquid in the beaker. After a few seconds a foam forms, which becomes finer and more homogeneous as time goes on. After 90 seconds the brush is removed. In the beaker is a stiff, homogeneous foam whose bubbles are in the main part invisible to the naked eye (a "microfoam"). The beaker may be inverted for a few seconds without the foam falling out. 30 ml of the foam is then drawn out of the beaker using a syringe for use in the treatment of a human patient's varicose veins using methodology which is generally known in this field.

The invention claimed is:

1. A foam comprising a liquid phase and a gas phase wherein the liquid phase comprises at least one sclerosing agent and the gas phase comprises from 41% to 100% of xenon.

2. A foam of claim 1 wherein the gas phase further comprises oxygen, carbon dioxide or a mixture of oxygen and carbon dioxide.

3. A foam of claim 1 wherein the sclerosing agent is polidocanol.

4. A method of treating varicose veins comprising injecting into a vein in need thereof a foam of claim 1.

5. A method of claim 4 wherein a greater saphenous vein is treated in one injection.

6. A method of claim 4 wherein between 15 ml and 50 ml of the foam is injected.

* * * * *